United States Patent [19]

Brandes

[11] Patent Number: 5,863,912

[45] Date of Patent: *Jan. 26, 1999

[54] METHOD OF TREATMENT OF HORMONE-UNRESPONSIVE METASTIATIC PROSTATE CANCER

[75] Inventor: Lorne J. Brandes, Winnipeg, Canada

[73] Assignee: Manitoba Cancer Treatment and Research Foundation, Winnipeg, Canada

[ * ] Notice: The term of this patent shall not extend beyond the expiration date of Pat. No. 5,432,168.

[21] Appl. No.: 666,351

[22] PCT Filed: Dec. 7, 1994

[86] PCT No.: PCT/CA94/00676

§ 371 Date: Sep. 5, 1996

§ 102(e) Date: Sep. 5, 1996

[87] PCT Pub. No.: WO95/17887

PCT Pub. Date: Jul. 6, 1995

[51] Int. Cl.[6] ..................................................... A01N 43/46
[52] U.S. Cl. ........................ 514/212; 514/317; 514/428; 514/649; 514/651; 514/217; 514/225.8; 514/226.2; 514/252; 514/255; 514/274; 514/296; 514/322; 514/325; 514/326; 514/397; 514/400; 514/460

[58] Field of Search ...................................... 514/651, 649, 514/212, 317, 428

[56] References Cited

U.S. PATENT DOCUMENTS 5,432,168  7/1995  Brandes, L.J. ............................ 514/90

FOREIGN PATENT DOCUMENTS

WO 92/11035  7/1992  WIPO .

Primary Examiner—Zohrem Fay
Assistant Examiner—Dwayne C. Jones
Attorney, Agent, or Firm—Sim & McBurney

[57] ABSTRACT

Prostate cancer particularly hormone-unresponsive metastatic prostate cancer, is treated by cyclophosphamide or other normally substantially inactive agent. Potentiation of the anti-cancer activity and amelioration of cyclophosphamide-associated toxicity is achieved by an initial intravenous infusion of DPPE over an approximately one hour period prior to cyclophosphamide treatment.

22 Claims, No Drawings

METHOD OF TREATMENT OF HORMONE-UNRESPONSIVE METASTIATIC PROSTATE CANCER

This application is a 371 of PCT/CA94/00676, filed on Dec. 7, 1994.

FIELD OF INVENTION

The present invention relates to the treatment of prostate cancer.

BACKGROUND TO THE INVENTION

Cancer of the prostate is now the most commonly-diagnosed cancer in males. It is estimated that, in 1993, there will be 110,000 new cases of prostate cancer diagnosed in the U.S. alone, while 45,000 will die from this disease. Prostate cancer is now the third leading cause of all cancer-specific deaths in men between the ages of 55 and 74. It is projected that by the year 2000, a 90% increase in annual incidence of the disease and a 37% increase in annual mortality rates will be observed. Although prostate cancer may be a relatively indolent neoplasm in the elderly, the overall decrease in life span in patients with this disease is approximately 10 years.

Improvement in the treatment of prostate cancer has centered on early detection; in recent years, a screening test (prostate-specific antigen, or PSA), although not entirely specific, has increased the power to diagnose this disease in asymptomatic patients. Treatment of early prostate cancer in men under the age of 65 has focused on radical surgery and/or radiotherapy, but the impact of these aggressive approaches on overall survival remains debatable. The approach to treatment of men over the age of 65 historically has been more conservative, and is based on the ablation of testosterone production. This result is achieved by the administration of female hormones (estrogen) or by orchidectomy, often in combination with anti-androgen medication. More recently, luteinizing hormone-releasing hormone (LHRH) agonists have joined the hormonal armamentarium.

Hormone manipulation often may result in significant palliation of metastatic prostate cancer, with improvement of bone pain and other disease-associated symptoms, as well as a significant fall in PSA levels (usually indicative of a decrease in tumor mass). Despite initial improvement on hormonal treatment, a majority of patients with locally unresectable or metastatic disease will progress and fail to respond to further hormonal therapies. In this large group of patients, other forms of treatment are far less effective. Radiotherapy often may relieve the symptoms of bone pain, but is not curative. Over time, the disease will progress with a fatal outcome.

Over the last 20 years, there have been many attempts to treat metastatic non-hormonally responsive prostate cancer with cytotoxic chemotherapy drugs. The results have been uniformly unrewarding. For example, in a comprehensive review of chemotherapy trials published by Eisenberger in 1985, only 131 out of 1,683 (8%) evaluable patients treated with any form of chemotherapy had an objective response to treatment. The list of inactive agents is long and includes the drug cyclophosphamide. For example, Eisenberger's study revealed that none of 57 evaluable patients responded to cyclophosphamide as a single agent. When cyclophosphamide was combined with other drugs, including doxorubicin, 5-fluorouracil or cisplatinum, the overall objective response rate was 20 out of 142 patients (14%). Thus, the overall response to cyclophosphamide alone, or in combination with other agents, was only 20 out of 199 (10%). Recently, Smith el al reported a 40% response rate (4 of 10 patients) employing very high doses of cyclophosphamide (4.5 mg/M$^2$) administered every 2 weeks in combination with granulocyte macrophage stimulating factor (GM-CSF); the latter was administered to counteract the severe myelosuppressive effects of this high dose of cyclophosphamide. Although not specifically reported, these patients also likely would have experienced significant nausea and vomiting and total loss of hair because of the dose of cyclophosphamide employed.

Thus, the analysis of several studies involving over 200 patients suggests that conventional doses of cyclophosphamide, administered alone or in combination with other cytotoxic chemotherapy drugs, are largely ineffective in the treatment of patients with hormone-refractory metastatic prostate cancer. Higher doses may be effective, but are associated with severe bone marrow depression, requiring the concomitant use of GM-CSF.

SUMMARY OF INVENTION

Surprisingly, I have recently observed in several human patients with prostate cancer that, when a conventional dose of cyclophosphamide (about 600 to 800 mg/M$^2$) is combined with the intracellular histamine receptor antagonist, N,N-diethyl-2-[4-(phenylmethyl)-phenoxy]ethanamine.HCl(DPPE; 240 mg/M$^2$), a marked potentiation of cyclophosphamide anticancer activity is observed. Conversely, cyclophosphamide-associated toxicity, including nausea, vomiting, alopecia (hair loss) and bone marrow depression, has been observed to be minimal. Thus, DPPE increases the therapeutic index of cyclophosphamide in patients with prostate cancer both by increasing the anticancer properties of cyclophosphamide to prostate cancer cells and by decreasing cyclophosphamide-associated host toxicity.

Accordingly, the present invention provides a novel method for the treatment of prostate cancer employing a normally-inactive chemotherapeutic agent for prostate cancer and a compound which inhibits normal cell proliferation while promoting malignant cell proliferation, used in an amount sufficient to inhibit the binding of intracellular histamine in normal cells, preferably an antagonist of intracellular histamine binding.

In one aspect, therefore, the present invention provides a method for the treatment of prostate cancer, which comprises administering to a human having prostate cancer, particularly hormone-unresponsive metastatic prostate cancer, a compound which inhibits normal cell proliferation while promoting malignant cell proliferation, particularly a potent antagonist for intracellular histamine receptors, in an amount sufficient to inhibit the binding of intracellular histamine in normal cells, and subsequently administering to the human an effective amount of a chemotherapeutic agent which is normally substantially inactive in the treatment of prostate cancer to effect potentiation of the anti-prostate cancer activity of said chemotherapeutic agent while minimizing chemotherapeutic agent-associated toxicity.

GENERAL DESCRIPTION OF INVENTION

In the present invention, any compound which is a potent antagonist of histamine binding at the intracellular histamine receptor is useful and is administered in an amount sufficient to inhibit the binding of intracellular histamine at the intracellular binding site ($H_{IC}$) in normal cells. Such compounds generally exhibit a pKi of at least about 5, preferably at least about 5.5.

Specific potent compounds which are useful in the present invention are diphenyl compounds of the formula:

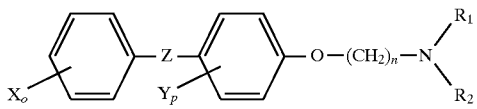

wherein X and Y are each fluorine, chlorine or bromine, Z is an alkylene group of 1 to 3 carbon atoms or =C=O, and p are 0 or 1, $R_1$ and $R_2$ are each alkyl groups containing 1 to 3 carbon atoms or are joined together to form a hetero-ring with the nitrogen atom and n is 1, 2 or 3. Pharmaceutically-acceptable salts of the diphenyl compounds may be employed.

Alternatively, the benzene rings may be joined to form a tricyclic ring, in accordance with the structure:

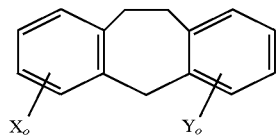

In one preferred embodiment, the group

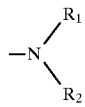

is a diethylamino group, although other alkylamino groups may be employed, such as dimethylamino, and, in another preferred embodiment, a morpholino group, although other heterocyclic ring groups may be employed, such as piperazino. o and p are usually 0 when Z is an alkylene group and n may be 2. In one particularly preferred embodiment, Z is —$CH_2$—, n is 2, o and p are each 0 and

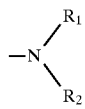

is a diethylamino group. This compound, namely N,N-diethyl-2-[4-(phenylmethyl)-phenoxy]ethanamine, in the form of its hydrochloride salt, is abbreviated herein as DPPE. In addition to a methyl group linking the benzene rings, other linking groups may be employed, such as =C=O. Other substitutions may be made on the benzene rings in addition to the halogen atoms, for example, an imidazole group.

The compounds used herein are potent antagonists of intracellular histamine binding at a site designated $H_{IC}$. Such compounds, in an intracellular histamine binding assay, generally exhibit pki values of at least about 5, preferably at least about 5.5. For example, DPPE exhibits a pki value of 6.5. The present invention employs compounds which potently and preferentially bind to $H_{IC}$.

The antagonist compound employed in the present invention is administered to the patient by intravenous injection of a solution thereof in an aqueous pharmaceutically-acceptable vehicle.

The antagonist compound is administered to the patient over a suitable period of time before administration of the chemotherapeutic agent. The chemotherapeutic agent or a mixture of such agents may be administered in any convenient manner consistent with its normal manner of administration following conventional chemotherapeutic practice, often by intravenous infusion of a solution thereof.

The administration of the antagonist compound to the patient prior to administration of the chemotherapeutic agent is necessary in order to permit the antagonist to inhibit the binding of intracellular histamine in normal and malignant cells and thereby, in effect, shut down proliferation of the normal cells, but increase proliferation of malignant cells.

The length of time prior to administration of the chemotherapeutic agent that the antagonist compound is administered depends on the antagonist compound, its mode of administration and the size of the patient. Generally, the antagonist compound is administered to the patient for about 30 to about 90 minutes, preferably about 60 minutes, prior to administration of the at least one chemotherapeutic agent.

In general, depending on the pKi of the antagonist, the quantity of compound employed in humans is from about 8 to about 320 mg/$M^2$ of animal to which the antagonist compound is administered, with about 240 mg/$M^2$ being the optimal DPPE dose for gastro-intestinal, hair and bone marrow protection. Over this dose range, the present invention is able to achieve an enhanced chemotherapeutic effect on prostate cancer cells while, at the same time, also protecting normal cells from damage by the chemotherapeutic agent in a wide variety of circumstances where traditional chemotherapy leads to damage of normal cells or tissues not involved in the disease process. Examples of the most common adverse effects on normal cells which result in traditional chemotherapy include:

(a) the killing of, or damage to, bone marrow cells,
(b) the killing of, or damage to, normal cells lining the gastrointestinal tract, and
(c) loss of hair In cancer-bearing animals, DPPE treatment alone modulates tumor growth with promotion at lower doses and inhibition (cytotoxicity) at higher doses. However, when combined with known anti-cancer drugs in the manner described herein, a marked synergistic action is observed whereby tumors are inhibited or killed by the anti-cancer drugs. This effect has led, for example, to marked regressions or cures in some animal, including human, cancers, such as sarcoma and melanoma.

As noted above, continued administration of the antagonist compound following administration of the chemotherapeutic agent at least ameliorates, and often eliminates, the side effects often associated with chemotherapy, including nausea, vomiting, anorexia and stomatitis, and preferably is effected herein, with the longer the period of administration, the more significant is the protection against the side effects. A daily dose of about 240 to about 1200 mg/$M^2$ of DPPE affords maximum bone marrow protection and synergy with chemotherapy to kill cancer cells.

Such continued administration of antagonist component is most conveniently effected by intravenous administration.

It has also been found that DPPE alone at low doses directly stimulates tumor cell growth in vivo and also increases the inflammatory response in skin elicited by the tumor promoting phorbol ester, PMA (phorbol myristate acetate). Several other classes of compounds, such as antidepressants, phenothiazines, triphenylethylene estrogens, histamine ($H_1$, $H_2$, $H_3$) antagonists, serotonin ($5HT_1$, $5HT_3$) antagonists, β-andrenergic antagonists and imidazole analogs, also have been identified as producing the same results as observed for DPPE.

It now also has been found that tricyclic antidepressant drugs and the non-tricyclic agent, fluoxetine (Prozac™), as well as $H_1$-antihistamine and β-adrenergic antagonists, also compete for the binding of $^3$H-DPPE and $^3$H-histamine to $H_{IC}$ in rat liver microsomes or brain membranes and, likewise, promote tumor growth.

Such compounds mimic the profiles of DPPE to inhibit normal cell proliferation but to promote malignant cell proliferation. Accordingly, these materials, at the proper dose level, could be predicted to increase the therapeutic index of chemotherapy drugs and are included within the scope of this invention.

Accordingly, in another aspect, the present invention provides a method for the treatment of prostate cancer wherein a compound which inhibits normal cell proliferation while promoting malignant cell proliferation is combined with chemotherapy agents to increase the therapeutic index of chemotherapy drugs, in like manner to DPPE and similar potent antagonists of intracellular histamine binding as specifically described herein.

Among the various compounds which may be employed in this aspect of the present invention are included:
 (a) tricyclic antidepressants, such as amitriptyline, clomipramine and imipramine,
 (b) non-tricyclic depressants, such as fluoxetine,
 (c) phenothiazines, such as prochloroperazine, trifluoroperizine and chlorpromazine,
 (d) $H_1$ antagonists, such as loratadine, hydroxyzine, phenyltoloxamine and astemizole,
 (e) β-adrenergic agonists and antagonists, such as propanolol,
 (f) serotonin ($5HT_1$ or $5HT_3$) antagonists, such as ondansertron ($5HT_3$) and cyproheptadine ($5HT_1$),
 (g) imidazoles and imidazole-like compounds, including $H_2$ antagonists, such as cimetidine and ranitidine, $H_3$ antagonists, such as thioperamide and antifungal agents, such as ketoconazole, and
 (h) triphenylethylene derivatives, such as tamoxifen.

In general, the compounds which may be employed in this aspect of the invention may have a chemical structure consisting of at least two phenyl rings, linked by a rigid third phenyl or non-phenyl ring, or by a non-rigid methyl, oxygen or other moiety, with the phenyl ring structure being linked by an ether, sulfhydryl or other ring structure or group to a basic alkylamine, imidazole or amino-imidazole side chain, for example, the carboxyamide-amino-imidazole L651582.

Although this wide range of compounds may be employed to increase the therapeutic index of chemotherapy drugs, DPPE and its direct analogs, may be significantly better agents for combination with chemotherapy than the foregoing groups of compounds, since DPPE appears to be more potent and selective for $H_{IC}$ and does not interact with calmodulin, protein kinase C or calcium channels and is only a weak antagonist at other common receptors, such as $H_1$, 5HT and $D_2$.

For example, DPPE does not cause serious cardiovascular effects in humans at clinically relevant doses to enhance chemotherapy, whereas, for example, at their relevant concentrations to antagonize $H_{IC}$, the antidepressant group of drugs and histidinol may cause cardiac arrythmias, $H_1$ antagonists may cause heart block and phenothiazines may cause significant hypertension.

The inhibitors to intracellular binding are employed in combination with anti-neoplastic agents which normally are ineffective in the treatment of prostate cancer, particularly hormone-unresponsive metastatic prostate cancer, to effect potentiation of the therapeutic index of such agent. In particular, the anti-neoplastic agent is cyclophosphamide, although others compounds useful in the present invention include ifosphamide, 5-fluorouracil, doxorubin and cis-platinum.

Such cyclophosphamide generally is used in dosage amounts which are conventional for cancer treatment or the treatment of solid tumors, usually in the range of about 600 to about 800 mg/$M^2$, although other useful quantities may be employed.

In one particular embodiment of the invention, the cyclophosphamide is used with DPPE as the antagonist of intracellular histamine, generally in an amount of about 240 mg/$M^2$. At such dosage level, a marked potentiation of cyclophosphamide anticancer activity towards prostate cancer is observed while cyclophosphamide-associated toxicity is minimized.

Preferably, the cyclophosphamide/DPPE treatment is effected by providing an intravenous infusion of an aqueous solution of DPPE over an 80 minute period, with cyclophosphamide being infused over the last 20 minutes of the DPPE infusion. The total quantities infused during this period correspond to the overall desired treatment level, as outlined above.

In general, multiple treatments by the combination of cyclophosphamide and DPPE is required to achieve remission of the prostate cancer. Treatment following the above regimen may be carried out for six successive weeks and then every two out of three weeks until the patient has achieved a complete remission, or may be continued as required in patients achieving partial remission or improvement, in the absence of complete remission.

EXAMPLES

The invention is illustrated further by the following three case studies:

CASE 1:

Following complaints of increased urinary frequency, a 65-year-old man was found, in December, 1987, to have an enlarged hard prostate. A biopsy showed infiltrating adenocarcinoma (Gleason grade not stated). He was treated with radical radiotherapy in April, 1988.

He remained well until August, 1990, when the PSA was elevated at 125 (normal value=1 to 4). A bone scan showed soft tissue uptake of isotope in the right upper quadrant, suspicious for liver metastases. A CT scan of the abdomen on Aug. 14, 1990, showed multiple large metastases within the liver. Biopsy of a liver lesion showed poorly differentiated carcinoma, compatible with metastatic prostate cancer. He was placed on an antiandrogen, Androcur 50 mg b.i.d, and on the estrogen, stilbesterol, 0.1 mg od. The PSA decreased to 44 on July 17, and to 26 on Dec. 14, 1990. Despite this, a CT scan did not show improvement. He remained on Androcur and stilbesterol. A repeat CT scan on Mar. 22, 1991, suggested some progression of the hepatic metastases. By June, 1991 his PSA climbed to 60, then to 116 on Sep. 27, 1991. He began to experience liver pain.

He was treated with bilateral orchidectomy on Nov. 8, 1991, and commenced on a different antiandrogen, flutamide, 250 mg t.i.d. His liver, which had enlarged to the point where he felt uncomfortable, started to decrease. By February, 1992, his PSA decreased to 5, and his liver decreased in size. A CT scan on Oct. 15, 1992, showed overall improvement in the metastases; the PSA was 1.7. He continued on flutamide, but, by July, 1993, his liver started to enlarge again and his PSA increased to 37.5.

The flutamide was discontinued. A CT scan showed extensive disease in his liver. The PSA was in the range of 40. The liver span was 15 cm; the liver edge was easily palpable 8 cm below the costal margin. He commenced weekly DPPE (240 mg/M$^2$) and cyclophosphamide (800 mg/M$^2$), on Aug. 13, 1993. Within 3 treatments, his liver pain resolved. The alkaline phosphatase decreased from 174 on July 16 to 100 on October 7. The LDH dropped from 445 to 220, the PSA decreased from 40 μg/L at the start of therapy to 33 μg/L on October 1st to 21 μg/L, on October 14. The liver span decreased to 13.5 cm; the liver edge was no longer palpable. The patient was able to lay on his right side without any discomfort, gained approximately 2 kg within 3 months) and was able to resume work. A repeat CT scan showed a significant decrease in the size of the liver metastasis. He remains on weekly DPPE/cyclophosphamide and has had no significant hair loss or bone marrow depression.

CASE 2:

This 75-year-old retired physician was well until the winter of 1992. While vacationing in California, he became very tired and felt mildly nauseated. He was found to have a PSA of approximately 1,800 and underwent prostatic biopsy which showed a diffuse adenocarcinoma of the prostate (Gleason score=9). He was treated with monthly injections of an LHRH agonist (Zoladex) and the anti-androgen, flutamide, 250 mg t.i.d. He stopped the flutamide after 3 weeks of therapy because of side effects, but continued on with Zoladex, monthly by injection. The PSA rapidly decreased to 3.2. He continued to do well on monthly Zoladex injections and recommenced flutamide on a b.i.d. schedule.

By August, 1993, he started once again to feel tired and unwell. He did not have any bone pain. The PSA level was now 568. A bone scan showed diffuse uptake; skeletal survey showed sclerosis in his right innominate bone and in various vertebrae. He complained of easy satiety and mild nausea. Over the next six weeks, the PSA climbed to 830.

The Zoladex and flutamide were discontinued. He commenced DPPE (240 mg/M$^2$) and cyclophosphamide (800 mg/M$^2$) therapy on Sep. 7, 1993. Within 12 hours of his treatment, he developed severe diffuse bone pain in his pelvis and back, which persisted for 72 hours; he required codeine every 4–6 hours for pain control. He was admitted to hospital 5 days later because of persisting weakness. Following rehydration and the administration of dexamethasone (10 mg/day) he rapidly improved. Within 48 hours, he was treated again with DPPE and cyclophosphamide, with little if any bone pain thereafter. The PSA dropped from 830 to 250 after the second treatment. He continued on DPPE/cyclophosphamide 2 out of every 3 weeks. Currently, he has no bone pain, his energy and appetite have improved, and the PSA, has declined, the most recent level being 45 on Nov. 29, 1993. A repeat bone scan showed almost complete resolution of metastasis. He has had no significant hair loss or bone marrow depression.

CASE 3:

This 61-year-old executive was diagnosed with Gleason 3–4 carcinoma of the prostate in October, 1989. Staging showed no spreading beyond the prostate gland. Acid phosphatase was slightly elevated at 0.91. He underwent radical prostatectomy; histology showed involvement of the right pelvic lymph nodes and seminal vesicles with tumor extending to the margin of resection. The patient had post-surgical radiotherapy between September and December 1989.

He remained reasonably well, but on May 25, 1990, the PSA (normal value=1–4) was found to be elevated at 5.5; it increased to 18 by August, 1990. In November, 1990, he started to have chest and rib pain. A bone scan showed multiple bony metastases. The patient underwent bilateral orchidectomy and commenced flutamide 250 mg t.i.d. in October, 1990. By March, 1991, the PSA was 0.4 and the bone scan showed improvement. However, in November, 1991, the PSA started to rise (6.4) but the patient continued to feel well.

By January, 1992, the PSA increased to 19. Despite the fact that he was asymptomatic, a bone scan on Mar. 6, 1992, showed worsening of his metastatic disease with intense focal uptake in the left sacroiliac joint, adjacent iliac bone and multiple other sites. He remained off therapy, but by July, 1992, began to have increasing bone pain requiring the regular use of codeine. He developed a hard fusiform swelling behind the right knee. The patient was started on the experimental imidazole analogue, R85246. He responded temporarily to this medication, but developed increasingly severe bone pain, as well as proliferative changes in his nail beds.

On Jun. 7, 1993, he started therapy with DPPE and cyclophosphamide. Following the first course of this therapy, he had a marked flare in bone pain which lasted for approximately 72 hours, accompanied by an increase in PSA from a pretreatment level of 107 to 262. After his second treatment, his bone pain almost completely subsided. By the end of the third DPPE/cyclophosphamide, he was totally off his codeine and had no further bone pain; the PSA dropped to 148 on Jul. 20, 1993. His nail beds resolved. Two bone scans 8 weeks apart showed stability, with no new lesions; the second scan suggested decreased uptake in various lesions as compared to previously. The fusiform hard swelling behind the right knee decreased from 12 cm$^2$ to 7.5 cm$^2$ (CT scan). He has continued on with DPPE/cyclophosphamide treatment, now reduced to two out of three weeks, has continued to be free of bone pain and has been able to resume work. He has had no significant hair loss or bone marrow depression.

SUMMARY OF DISCLOSURE

In summary of this disclosure, the present invention provides a method of treatment of prostate cancer, combining an antagonist of intracellular histamine binding with a conventional dose of a normally inactive agent, particularly cyclophosphamide. A specific example is the combination of DPPE (240 mg/M$^2$) infused intravenously over 80 minutes with cyclophosphamide (600–800 mg/M$^2$) infused over the last 20 minutes of the DPPE infusion. This treatment is continued weekly for six weeks and then every 2 out of 3 weeks, until the patient has achieved a complete remission, or continued as required in patients achieving partial remission or improvement, in the absence of complete remission. The novel method provided herein provides a significant amelioration of cyclophosphamide-associated side effects, namely bone marrow suppression and alopecia. Other intracellular histamine antagonists may be used in combination with cyclophosphamide, as described for DPPE. Modifications are possible within the scope of this invention.

What I claim is:

1. A method for the treatment of prostate cancer, which comprises:

administering to a human having prostate cancer a compound which inhibits normal cell proliferation while promoting malignant cell proliferation in an amount sufficient to inhibit the binding of intracellular histamine in normal cells by the intravenous injection of a solution thereof in an aqueous pharmaceutically-acceptable vehicle, and subsequently administering to said human an effective amount of a chemotherapeutic agent which is normally substantially inactive in the treatment of prostate cancer to effect potentiation of the anti-prostate cancer activity of said chemotherapeutic agent while minimizing chemotherapeutic agent-associated toxicity.

2. The method of claim 1 wherein said prostate cancer is hormone-unresponsive metastatic prostate cancer.

3. The method of claim 2 wherein said chemotherapeutic agent comprises cyclophosphamide, ifosphamide, 5-fluorouracil, doxorubin or cis-platinum.

4. The method of claim 3 wherein said chemotherapeutic agent is cyclophosphamide.

5. The method claimed in claim 4 wherein said compound is a potent antagonist for intracellular histamine receptors.

6. The method of claim 5 wherein said potent antagonist selective for intracellular histamine receptors is a diphenyl compound of the formula:

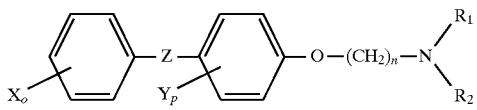

wherein X and Y are each fluorine, chlorine or bromine, Z is an alkylene radical of 1 to 3 carbons or a =C=O group, or the phenyl groups are joined to form a tricyclic ring, o and p are 0 or 1, $R_1$ and $R_2$ are each alkyl groups containing 1 to 3 carbon atoms or are joined together to form a hetero-ring with the nitrogen atom and n is 1, 2 or 3, or a pharmaceutically-acceptable salt thereof.

7. The method of claim 6 wherein the group

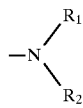

is a diethylamino group, a dimethylamino group, a morpholino group, or a piperazino group.

8. The method of claim 6 wherein the group

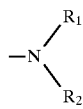

is a diethylamino group, Z is —CH$_2$—, n is 2, and o and p are each 0.

9. The method of claim 8 wherein the diphenyl compound is in the form of a hydrochloride salt.

10. The method of claim 5 wherein said antagonist is administered to the animal by intravenous infusion about 30 to about 90 minutes prior to said administration of said cyclophosphamide.

11. The method of claim 10 wherein the time is about 60 minutes.

12. The method of claim 11 wherein said antagonist is administered in an amount of about 240 mg/M$^2$ of animal while said cyclophosphamide is employed in an amount of from about 600 to about 800 mg/M$^2$.

13. The method of claim 12 wherein said administrations are effected weekly for six successive weeks and then every two out of three weeks until the patient has achieved complete remission, or is continued as required in patient's achieving partial remission.

14. The kit of claim 13 wherein said compound which inhibits normal proliferation is a potent antagonist for intracellular histamine receptors for component (a).

15. The kit of claim 14 wherein said potent antagonist selective for intracellular histamine receptors is a diphenyl compound of the formula:

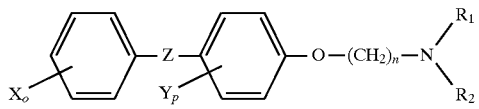

wherein X and Y are each fluorine, chlorine or bromine, Z is an alkylene radical of 1 to 3 carbon atoms or a =C=O group, or the phenyl groups are joined to form a tricyclic ring, o and p are 0 or 1, $R_1$ and $R_2$ are each alkyl groups containing 1 to 3 carbon atoms or are joined together to form a hetero-ring with the nitrogen atom and n is 1, 2 or 3, or a pharmaceutically-acceptable salt thereof.

16. The kit of claim 15 wherein the group

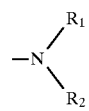

is a diethylamino group, a dimethylamino group, a morpholino group, or a piperazino group.

17. The kit of claim 15 wherein the group

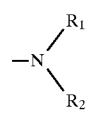

is a diethylamino group, Z is —CH$_2$—, n is 2, and o and p are each 0.

18. The kit of claim 17 wherein the diphenyl compound is in the form a hydrochloride salt.

19. A kit for the treatment of prostate cancer in humans, comprising:

(a) a first component consisting of a compound which inhibits normal cell proliferation while promoting malignant cell proliferation in a dosage amount sufficient to inhibit binding of intracellular histamine in normal cells in the human, and, separately, (b) a second component consisting of a chemotherapeutic agent which is normally substantially inactive in the treatment of prostate cancer in a dosage amount toxic to said prostate cancer cells when administered to the human subsequent to administration of said first component to the human.

20. The kit as claimed in claim 19, wherein said chemotherapeutic agent is cyclophosphamide, ifosphamide, 5-fluorouracil, doxorubin or cis-platinum for component (b).

21. The method of claim 9 wherein said antagonist is administered to the animal by intravenous infusion over a period of about 30 to about 90 minutes prior to administration of said cyclophosphamide by intravenous infusion while intravenous infusion of said antagonist is maintained.

22. The method of claim 21 wherein said intravenous infusion of said antagonist is effected for a total of about 80 minutes to administer a total amount of about 240 mg/M$^2$ of said antagonist while said intravenous infusion of cyclophosphamide is effected over the last about 20 minutes of said intravenous infusion of said antagonist to administer about 600 to 800 mg/M$^2$ of cyclophosphamide.

* * * * *